(12) United States Patent
Hirt et al.

(10) Patent No.: US 11,751,883 B2
(45) Date of Patent: Sep. 12, 2023

(54) FIXING SYSTEM AND ALIGNING DEVICE

(71) Applicant: Aesculap AG, Tuttlingen (DE)

(72) Inventors: Martin Hirt, Stockach (DE); Stephan Lindner, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 176 days.

(21) Appl. No.: 17/296,830

(22) PCT Filed: Nov. 28, 2019

(86) PCT No.: PCT/EP2019/082964
§ 371 (c)(1),
(2) Date: May 25, 2021

(87) PCT Pub. No.: WO2020/109502
PCT Pub. Date: Jun. 4, 2020

(65) Prior Publication Data
US 2022/0008086 A1    Jan. 13, 2022

(30) Foreign Application Priority Data

Nov. 28, 2018 (DE) ..................... 10 2018 130 119.7

(51) Int. Cl.
*A61B 17/15* (2006.01)
*A61B 90/50* (2016.01)
*A61B 17/00* (2006.01)

(52) U.S. Cl.
CPC ............ *A61B 17/157* (2013.01); *A61B 90/50* (2016.02); *A61B 2017/00876* (2013.01)

(58) Field of Classification Search
CPC ...... A61B 1/00158; A61B 2017/00876; A61B 17/1707; A61B 34/73; A61B 2034/731;
(Continued)

(56) References Cited

U.S. PATENT DOCUMENTS 4,621,628 A * 11/1986 Brudermann .......... A61B 17/72
606/97
5,002,547 A    3/1991 Poggie et al.
(Continued)

FOREIGN PATENT DOCUMENTS

DE    20105643 U1    6/2001
DE    69719663    11/2003
(Continued)

OTHER PUBLICATIONS

Written Opinion received in International Application No. PCT/EP2019/082960 dated Feb. 5, 2020, with translation, 13 pages.
(Continued)

*Primary Examiner* — Kevin T Truong
*Assistant Examiner* — Diana Jones
(74) *Attorney, Agent, or Firm* — Christopher A. Rothe; Culhane Meadows PLLC

(57) ABSTRACT

A fixing system for an aligning device of a tibial resection guide for fixating attachment to a limb and an aligning device having the fixing system. The fixing system includes a carrier device having an attachment portion for attaching to an adjustment rod, a fixing magnet arranged on a front side of the carrier device, and a magnetic band adapted to be attracted to the fixing magnet and adapted to be attached to the limb of a patient.

14 Claims, 4 Drawing Sheets

(58) Field of Classification Search
CPC .......... A61B 2034/732; A61B 2050/21; A61B 17/157; A61B 17/15; A61B 90/50
See application file for complete search history.

(56) References Cited

U.S. PATENT DOCUMENTS

| | | | |
|---|---|---|---|
| 5,049,151 A * | 9/1991 | Durham | A61B 17/1725 606/98 |
| 5,197,944 A | 3/1993 | Steele | |
| 5,514,145 A * | 5/1996 | Durham | A61B 17/1707 408/115 R |
| 5,628,750 A | 5/1997 | Whitlock et al. | |
| 5,667,511 A | 9/1997 | Vendrely et al. | |
| 5,704,941 A | 1/1998 | Jacober et al. | |
| 6,162,228 A * | 12/2000 | Durham | A61B 17/1707 606/96 |
| 6,221,035 B1 | 4/2001 | Kana et al. | |
| 6,277,123 B1 | 8/2001 | Maroney et al. | |
| 7,344,542 B2 | 3/2008 | Collazo et al. | |
| 7,785,330 B2 * | 8/2010 | Sherman | A61B 17/1707 606/104 |
| 10,792,049 B2 | 10/2020 | Fiedler et al. | |
| 2005/0070910 A1 | 3/2005 | Keene | |
| 2006/0189998 A1 | 8/2006 | Rasmussen | |
| 2006/0241639 A1 | 10/2006 | Kuczynski et al. | |
| 2008/0027471 A1 | 1/2008 | Hauri | |
| 2010/0087831 A1 | 4/2010 | Marx | |
| 2012/0053594 A1 | 3/2012 | Pelletier et al. | |
| 2012/0101504 A1 | 4/2012 | Habegger et al. | |
| 2014/0324054 A1 | 10/2014 | Dmuschewsky et al. | |
| 2016/0367291 A1 | 12/2016 | Erickson et al. | |
| 2017/0245893 A1 | 8/2017 | Sanders et al. | |
| 2022/0008086 A1 | 1/2022 | Hirt et al. | |
| 2022/0022889 A1 | 1/2022 | Hirt et al. | |
| 2022/0160370 A1 | 5/2022 | Boettinger et al. | |

FOREIGN PATENT DOCUMENTS

| | | |
|---|---|---|
| DE | 69531388 | 6/2004 |
| DE | 69630776 | 9/2004 |
| DE | 60028278 | 5/2007 |
| DE | 60212852 T2 | 8/2007 |
| DE | 102006035602 A1 | 2/2008 |
| DE | 202015101629 U1 | 7/2015 |
| DE | 102018130117 A1 | 5/2020 |
| DE | 102019103880 A1 | 8/2020 |
| EP | 0839501 A2 | 5/1998 |
| GB | 2398010 A | 8/2004 |
| JP | 2008125706 A | 6/2008 |
| JP | 2011092405 A | 5/2011 |
| WO | 0071035 A1 | 11/2000 |
| WO | 03013371 A1 | 2/2003 |
| WO | 2005110249 A1 | 11/2005 |
| WO | 2009037479 A1 | 3/2009 |
| WO | 2012027816 A1 | 3/2012 |
| WO | 2013134595 A1 | 9/2013 |
| WO | 2019046518 A2 | 3/2019 |
| WO | 2020013584 A1 | 1/2020 |
| WO | 2021209496 A3 | 10/2021 |

OTHER PUBLICATIONS

Written Opinion received in International Application No. PCT/EP2019/082964 dated Mar. 6, 2020, with translation, 9 pages.
Office Action received in Japanese Application No. 2021-546788 dated Feb. 25, 2022, with translation, 10 pages.
Search Report received in German Application No. 10 2019 103 880.4 dated Oct. 23, 2019, with translation, 16 pages.
Search Report received in International Application No. PCT/EP2020/053740 dated Oct. 9, 2020, with translation, 6 pages.
Written Opinion received in International Application No. PCT/EP2020/053740 dated Oct. 9, 2020, with translation, 9 pages.
Search Report received in German Application No. 10 2020 110 346.8 dated Dec. 11, 2020, with translation, 12 pages.
Search Report received in International Application No. PCT/EP2021/059647 dated Oct. 12, 2021, with translation, 10 pages.
Written Opinion received in International Application No. PCT/EP2021/059647 dated Oct. 12, 2021, with translation, 29 pages.
Non-Final Office Action received in U.S. Appl. No. 17/296,676, dated Mar. 28, 2022.
International Search Report received in International Application No. PCT/EP2019/082960 dated Feb. 5, 2020, with translation, 5 pages.
International Search Report received in International Application No. PCT/EP2019/082964 dated Mar. 6, 2020, with translation, 10 pages.
Search Report received in German Application No. 10 2018 130 117.0 dated Sep. 5, 2019, with translation, 14 pages.
Search Report received in German Application No. 10 2018 130 119.7 dated Sep. 5, 2019, with translation, 11 pages.

* cited by examiner

FIXING SYSTEM AND ALIGNING DEVICE

CROSS-REFERENCE TO RELATED APPLICATION(S)

This application is the United States national phase entry of International Application No. PCT/EP2019/082964, filed Nov. 28, 2019, and claims the benefit of priority of German Application No. 10 2018 130 119.7, filed Nov. 28, 2018. The contents of International Application No. PCT/EP2019/082964 and German Application No. 10 2018 130 119.7 are incorporated by reference herein in their entireties.

FIELD

The present invention relates to a fixing system for an aligning device of a tibial resection guide for fixing attachment to a body extremity/limb, such as an ankle, leg or tarsal joint, comprising a carrier device having an attachment portion for attachment to an adjustment rod. In addition, the invention relates to an aligning device/adjustment guide.

BACKGROUND

Precise resection of a patient's bone, especially of the tibia, is of great importance for the success of an operation for implanting a joint prosthesis. The plane of the resection must be precisely localized in order to minimize a degree of bone removal on the one hand, while at the same time ensuring that all defective bone tissue is removed. The alignment of the plane in relation to an anatomical axis, in particular a tibial axis, must be continuously monitored during surgery to ensure the alignment of the joint surfaces of the joint over the entire range of joint motion.

The exact definition of a tibial resection plane in a knee joint is usually set using an aligning device or adjustment guide (for a saw block) with a (columnar) adjustment rod, which is fixed away from the tibia close to the ankle. The adjustment rod extends along the tibia (essentially) parallel to the corresponding anatomical tibial axis. The resection plane can then be defined in relation to the tibial axis. A sawing block or guiding block (cutting block/guiding device) attached to the aligning device defines the plane of the resection. The guiding block usually has a slot through which a reciprocating, flat cutting edge of a surgical instrument (saw) is passed.

In order to adjust the alignment of the tibial resection plane, a fixation clamp is placed near the ankle, which is hinged to one end of the adjustment rod facing a patient's foot, to the other end (end portion) of which the saw/guide block is fixed/fixable.

In the prior art, various forms of an aligning device and an associated fixing clamp or fixing system are disclosed.

For example, US 2016/0367291 A1, for example, discloses an adjustment guide with two rod-shaped components, each of which has a ball joint at its end portions and is arranged substantially symmetrically to the tibial axis on the left and right of the foot or leg. A fixation clamp in the form of a U-shaped frame with screws drilled into the heel bone fixes the two rod-shaped components. The adjustment guide has a large number of adjustment possibilities for an alignment of a guiding block or guiding device. However, it is disadvantageous that bone substance is unnecessarily removed for fixation by screwing into the heel bone and healthy bone tissue is damaged. Also, the distal fixation cannot be subsequently changed and adjusted.

U.S. Pat. No. 6,221,035 B1 discloses a (fixation) clamp for an alignment aid used in tibial resection. The clamp has two spring-prestressed clamp arms, each of which can be rotated about an axis of rotation relative to a frame. These clamp arms are brought into an open position and, after contact with the tibia, are released by means of a manual release device. Due to the spring preload, they then enclose or grip around an ankle joint or the tibia and clamp it. The clamp arms are pretensioned in the closing direction. The spring preload causes a force-fit fixation, but this has the disadvantage that the clamping force can cause hematomas on the concerned sites on the patient's body. It is also not possible to adjust the clamping force.

US 2017/0245893 A1 also discloses an aligning device and an associated fixation device. Here, a screw is drilled through the heel bone in an embodiment to set a fixed point of the aligning device. CN 205379351 U also discloses an adjustment guide in which screws are screwed into foot bones for fixation.

U.S. Pat. No. 5,197,944 A discloses an orthopedic instrument and, in particular, an ankle clamp or fixation clamp that allows a surgeon to attach the ankle clamp to a patient with one hand as part of the tibial alignment assembly. In particular, this clamp has a locking feature that secures the movable arms of the clamp in an open position until the clamp is positioned for use, at which time the locking feature of the arms of the clamp can be released and the clamp is then firmly secured via pretensioning around the patient's ankle. In this regard, the arms are movable between an open and closed position and are pretensioned by springs to assume the closed position that grips the patient's ankle during use. To accomplish this, the arms feature a notched end portion located near the pivot point of the arm. This notch works in conjunction with a latch to secure the arms in an open position. The latch has an external pressure plate surface that can be manually pressed to release the latch from the respective moving arm.

However, one problem of the prior art is that the fixation to the patient's ankle is either only performed via force-fit or the clamp arms are pretensioned for force-fit and not fixed in a form-fit manner (resulting in insufficient positionability due to the resulting inherent elasticity of the clamp arms), or that screws have to be screwed into a (healthy) bone for fixation (which puts additional strain on the patient and also increases the risk of infection). In the case of the force-fit connection, this leads to a detachable fixation, which, however, is insufficient due to the high requirements for dimensional accuracy or accuracy to the alignment of the plane of the resection described at the beginning, and, in the case of fixation by means of screws, leads to further, unnecessary damage to the bone, which, however, should be prevented. In addition, the clamping force of elastically preloaded clamp arms can cause hematomas on the patient's body parts. Furthermore, fixation clamps of the prior art do not cover all anatomical sizes of patients, as the clamping force depends on the respective anatomy of the patient. Therefore, different variants of fixation clamps/fixation systems have to be manufactured and provided.

SUMMARY

It is the object of the invention to avoid or at least to reduce the disadvantages of the prior art and in particular to provide a fixing system as well as an aligning device which allows or which allow a simple, safe and fast fixation as well as a simple and fast release of the fixation of a body extremity/limb, in particular around the ankle joint or the tibia of the patient, wherein the fixing system is adapted for different anatomies of body extremities, in particular of the ankle joint, and can be used for any anatomy and avoids hematomas by its operation principle and configuration. In addition, the fixing system and the aligning device should be operable with only one hand.

The object of the invention is solved in a generic fixing system according to the invention in that the fixing system comprises a fixing magnet, which is arranged/attached to a front side or to a terminal/front side portion of the carrier device and together with the carrier device forms a magnetic carrier, and comprises a separately formed, in particular flexible, magnetic band, which or the front side of which is formed to attract the fixing magnet, so that the fixing magnet is detachably magnetically adhered to the front side of the magnetic band. The magnetic band is adapted to be attached to the limbs/body extremities of a patient and in particular has a convex curvature to form a diameter. Compared to the prior art, the fixing system according to the invention does not have clamp arms/clamp fingers or clamping systems, where hematomas can occur, and no fixation screws for fixation in bone tissue, but a, preferably flexible, magnetic band, which is attached to the intended body part and fixed there, and a complementary fixing magnet, which is detachably magnetically attached to the magnetic band. Attachment by means of magnetic force is a completely new variant of a fixing system. A magnetic band can have both a permanent magnetic material and a ferromagnetic material. Likewise, the fixing magnet can have a permanent magnetic material as well as a ferromagnetic material. The only decisive factor is that the magnetic band and the fixing magnet attract each other magnetically. This can be achieved in particular by either the magnetic band or the fixing magnet having a permanent magnetic material.

Instead of providing a fixing system with essentially only a single/indivisible assembly, which is realized according to the state of the art by means of the usual form-fitting wrapping around the ankle by means of spring-elastically pretensioned clamp arms or clamp fingers of a fixing clamp rigidly and firmly attached to an aligning device, the core of the present invention therefore consists in providing the user with a fixing system which is basically designed in at least two parts/with two components or assemblies, wherein one component (the magnetic band or the ferromagnetic metal band) of the fixing system is arranged and fixed to the patient's ankle in a form-fit, friction-fit and/or material-fit manner, and the other component (the magnet carrier) is attached to the aligning device. The two components thereby have a magnetic interaction or magnetic attraction, which is why they magnetically attract each other with a maximum magnetic force. This magnetic force is used to releasably connect the two components of the fixing system and consequently to position them against each other. Thus, the magnetic band as one component can be attached to the patient independently of the magnet carrier as the other component, and can be detached as well as repositioned and can remain on the patient, whereas the magnet carrier can be magnetically detached or connected in a force-fitting manner. This allows a magnetically determined simple, easy and fast attachment/fixation and detachment of the magnet carrier and thus of the aligning device to the (ankle joint of the) patient. The combination of a magnetic band and a magnet carrier as a magnetic counterpart is completely new. Hematomas are avoided and the magnetic band adapts anatomically to the patient. The fixing system provided can be operated quickly and easily with one hand.

In a first preferred embodiment, the magnetic band may be in the form of a magnetic slap wrap whose longitudinal axis, in a first state (open state), extends (substantially) along a straight line due to a geometric restriction against a pretension caused by a bend symmetrical to the longitudinal axis towards an outer side, and whose longitudinal axis, in a second state (snap state), after removal of the geometric restriction, reduces the pretension and winds spirally or helically around a limb and the magnetic slap wrappingly fixes it in a clamping, force-fitting manner.

Preferably, the magnetic slap wrap can have multiple flexible magnetic portions along its longitudinal axis. This extends a magnetic range and eliminates the need for precise alignment of the magnetic slap wrap, since several magnetic portions are present.

In particular, the slap wrap can have a length of at least 300 mm along its longitudinal axis so that it can wrap around an ankle over 360°. This ensures sufficient clamping force or, in addition to force-fit, also a form-fit and, in particular, ensures that there is a magnetically attracted surface all around the ankle.

In an alternative, second preferred embodiment, the magnetic band may be in the form of a magnetic foil, in particular a flexible magnetic foil, the rear side of which has an adhesive portion for adhesion to a body part of a limb. The adhesive portion thus enables quick fixation to a body part and, if the magnetic foil is designed to be flexible, the magnetic foil adapts anatomically to the corresponding body part. This means that a wide range of anatomies can be covered with just one magnetic foil. The magnetic foil offers the fixing magnet a surface for docking or magnetic attachment.

In a further, third alternatively preferred embodiment, the magnetic band can be in the form of a magnetic wrist band or magnetic foot band with a closure, which is attached to a limb by wrapping around it/encompassing it and can be closed and fixed by means of the closure. The closure can have different shapes. For example, the closure can be in the form of a watchband closure with a pin buckle that is positioned in the openings of the other watchband. The closure can also be designed as a click quick-release closure or as a clip closure. This makes it possible to fix the magnetic wrist band with different diameters or circumferences and different closure forces or fixing forces according to the choice of the tightness of the wrist band.

According to one aspect of the invention, the carrier device can have a carrier base with the attachment portion and a slider with the fixing magnet that can be moved translationally in a sliding direction V relative to the carrier base, in particular by means of a guide bar. In particular, the carrier base is T-shaped and the slider moves at the front side of the carrier base.

According to a further aspect of the invention, the carrier device may comprise a rotational adjustment mechanism/rotational device/rotational adjustment device which can be used for adjusting the position of the slider relative to the carrier base in the sliding direction V. In this way, a relative position between the carrier base and the slider can be set and maintained very precisely by simple means, in particular by means of a worm gear and an associated thread. In particular, the rotational adjustment mechanism has an external thread (worm gear) held axially fixed on one component, which engages in an internal thread on the other component.

Preferably, the carrier device can have a concave holder perpendicular to the longitudinal axis of the attachment portion, in which the fixation magnet is enclosed, so that in addition to the force-fit fixation, a form fit to the sides of a tibial axis is achieved. The holder further supports fixation and locks a degree of freedom transverse to the tibial axis.

In a preferred embodiment, the fixing magnet may be encased in a plastic layer so that the carrier device with the fixing magnet is readily sterilizable.

Preferably, the attachment portion is designed in the form of a rectangular cantilever which has a passage slit along its longitudinal axis in order to accommodate an adjustment rod to be (longitudinally) displaceable in the longitudinal direction. Thus, the attachment portion can also be symmetrical to an adjustment rod.

In particular, the attachment portion has notches or corrugations on its outer sides in order to be able to define a position relative to an adjustment rod by means of form fit.

In a generic aligning device for a tibial resection guide for use in preparing a knee joint for implantation of a prosthesis, with an adjustment rod which can be arranged at the tibia, and with a guiding device at the proximal end of the adjustment rod, in order to guide a tool during the resection of the tibia the object of the invention is solved according to the invention by providing a distal fixing system according to the invention, which is arranged at the distal end of the adjustment rod or towards the distal end of the adjustment rod. The aligning device can be quickly and easily aligned and arranged on a tibia or relative to a tibia of the patient via the fixing system according to the invention and can be released again just as easily in order to reposition or remove the aligning device. Handling is significantly simplified and hematomas are prevented.

BRIEF DESCRIPTION OF THE DRAWING FIGURES

The present invention is explained in more detail below by reference to preferred embodiments with reference to the accompanying figures.

The figures are schematic in nature to aid understanding of the invention. Identical elements are provided with the same reference signs. The features of the different embodiments can be interchanged.

DETAILED DESCRIPTION

Figure 1:
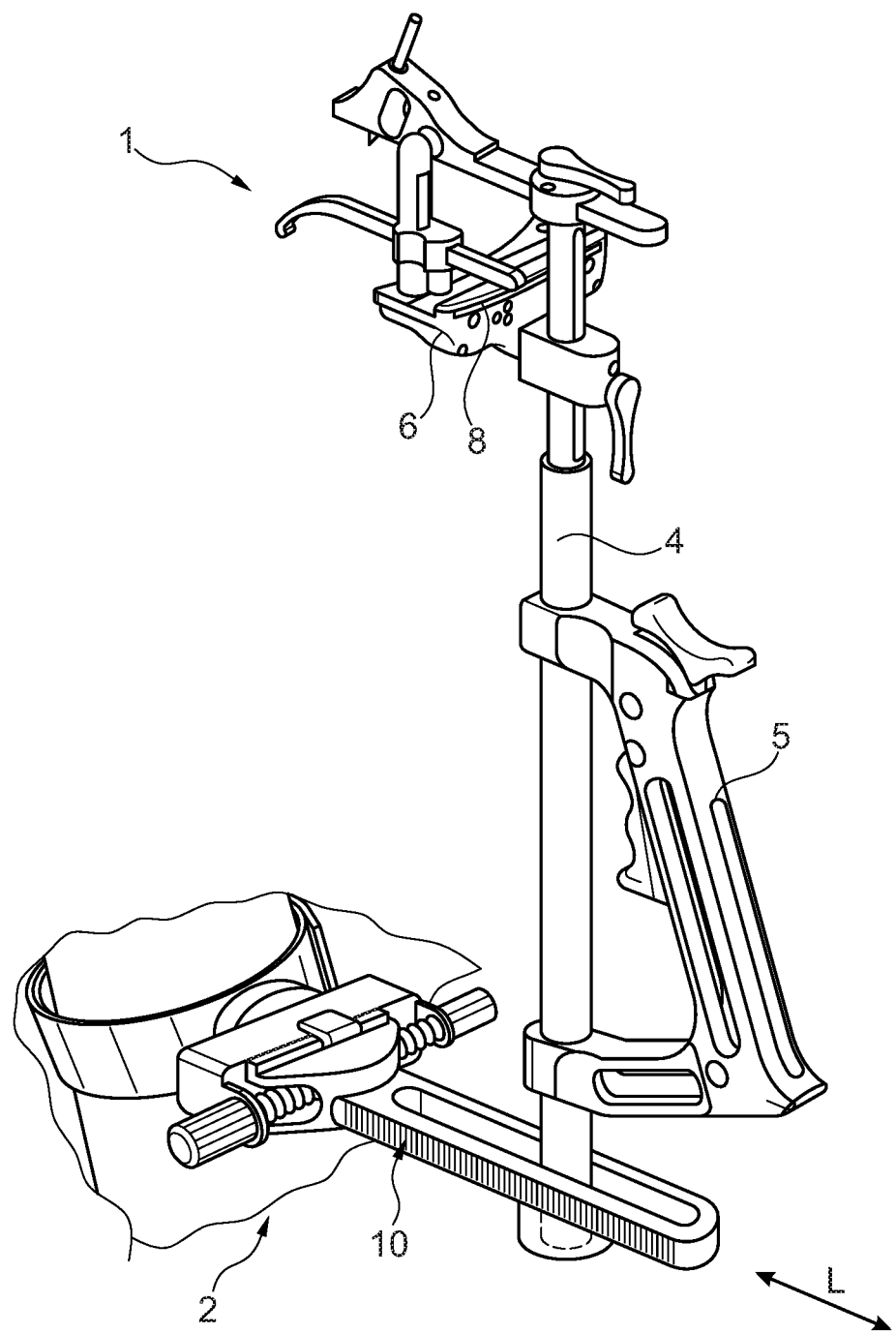
FIG. 1 shows a perspective view of an aligning device according to the invention of a preferred embodiment.

FIG. 1 shows a perspective view of an aligning device 1 of a preferred embodiment according to the invention for a tibial resection guide for use in preparing a knee joint for implantation of a knee joint prosthesis with a fixing system 2 of a first preferred embodiment according to the invention.

The aligning device 1 has a length-adjustable telescopic rod 4 with a handle 5 rigidly mounted thereon so that the telescopic rod 4 can be aligned with respect to a tibia of a patient (not shown). At one end of the telescopic rod 4, which faces the thigh when aligned with the patient, a (tool) guiding device 6 in the form of a (saw) block with a planar passage slit or passage opening through the block as a cutting gap or guiding gap 8 is attached, through which a tool can be inserted or passed. The (plane) cutting gap 8 defines the plane of the resection. The fixing system 2 according to the invention, which is described in detail below with reference to FIGS. 2 to 7, is hinged or fastened to an end of the telescopic rod 4 opposite the guiding device 6, which, when aligned with the patient, points towards the foot. The fixing system 2 serves to define a fixed point for the aligning device 1 and for this purpose grips/encompasses an ankle of the patient.

The fixing system 2 has a block-shaped cantilever/cantilever beam 10 as an attachment portion for attaching/fastening/mounting to the telescopic rod 4. The cantilever 10 has a passage opening along its longitudinal axis L in the form of a passage slit 22, whereby the end of the telescopic rod 4 facing the foot protrudes into or through the passage slit 22 and thereby preferably elastically presses apart the two clips of the cantilever 10 formed by the passage slit 22. Due to the geometric interaction, the fixing system 2 can be translationally displaced longitudinally with respect to the adjustment rod 4 in order to adjust a position in the sagittal plane or an offset between the fixing system 2 and the guiding device 8. Furthermore, the cantilever 10 can be equipped with an (additional) pretensioning device (shown symbolically at the free end of the cantilever 10), via which the clamping force of the two clips of the cantilever 10 on the telescopic rod 4 clamped by them can be further increased.

As can be seen from FIG. 1, a number of operating devices (operating buttons/operating wheels) can be provided on the handle 5, by means of which, for example, functions of the telescopic rod 4 can be activated.

FIGS. 2 to 5 show the fixing system 2 according to the invention in accordance with the first preferred embodiment. The fixing system 2 has essentially two components. One component or assembly is a magnet carrier 11 with a T-shaped carrier device 12 and with a fixing magnet 14 attached to the end face, and the other component or assembly is a magnetic band in the form of a slap wrap 16, the front face of which is designed to be magnetically attracted to the fixing magnet 14, in particular by the slap wrap 16 being coated with a magnetic material or by magnetic material being inserted in the slap wrap 16 as an inlay or intermediate layer.

Figure 2:
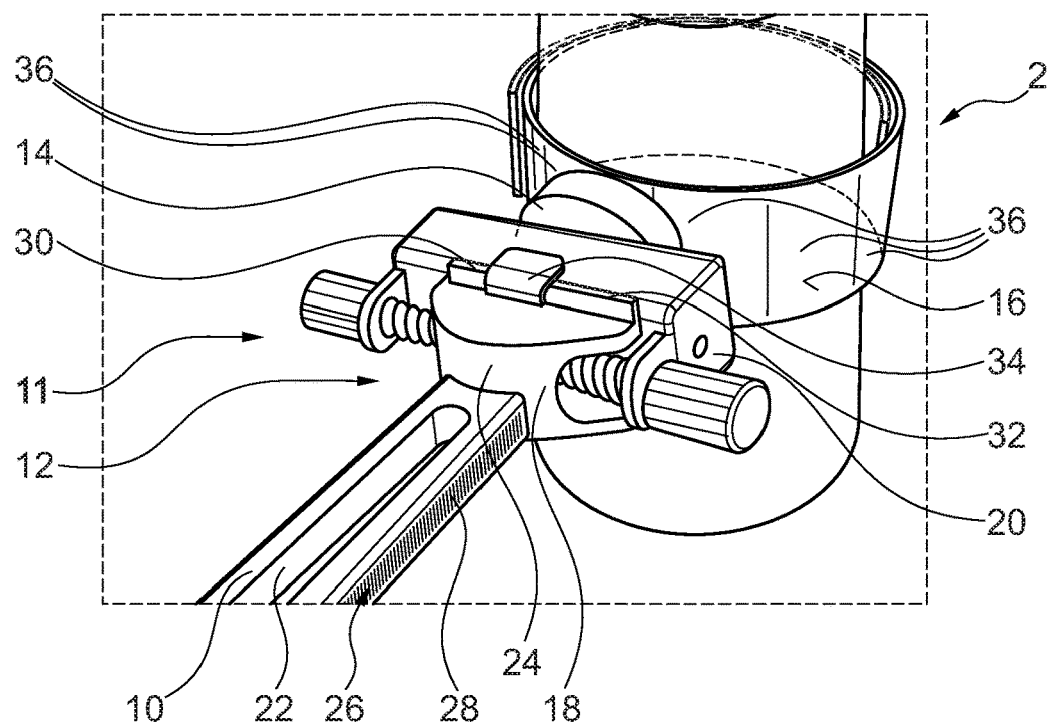
FIG. 2 shows a perspective view of a fixing system according to the invention of a first preferred embodiment.
Figure 3:
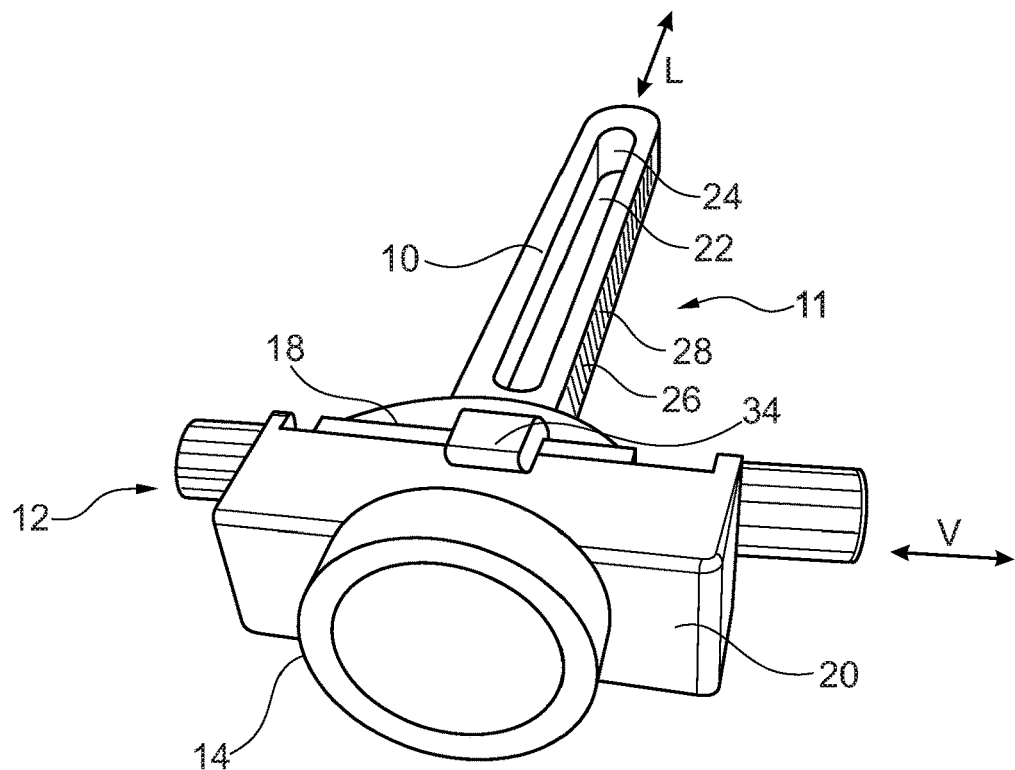
FIG. 3 shows a perspective view of the fixing system from FIG. 2.
Figure 4:
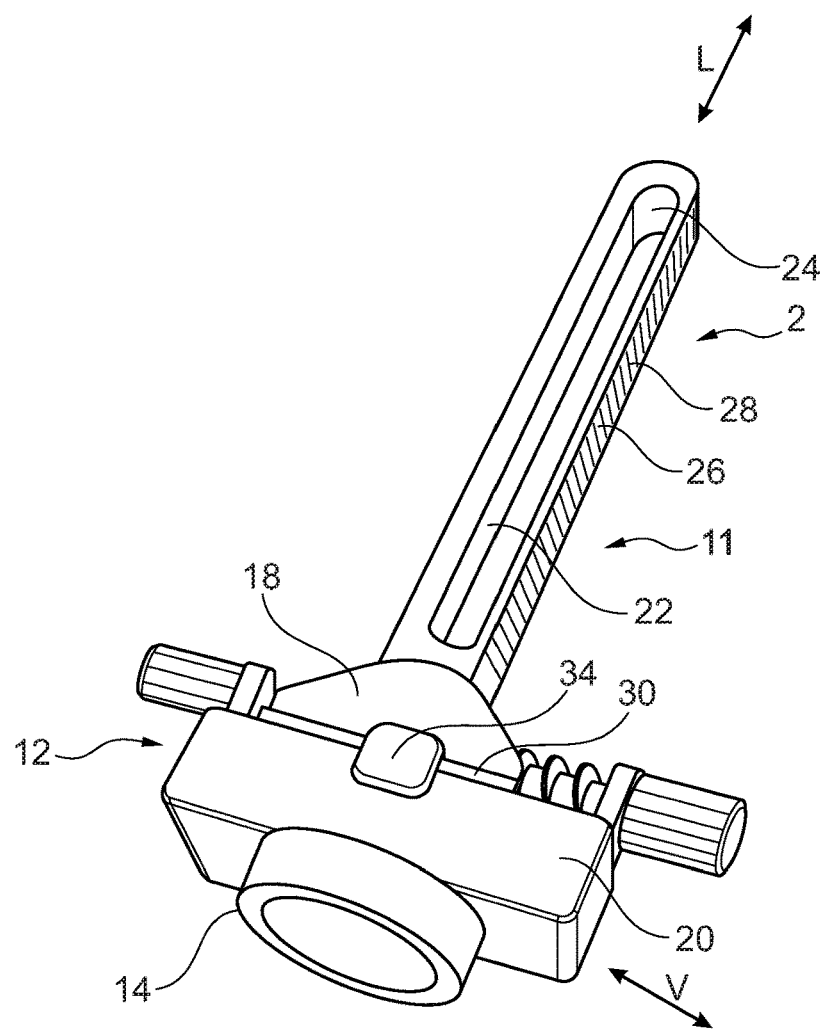
FIG. 4 shows a further perspective view of the fixing system from FIG. 2 and FIG. 3.

First, the magnet carrier 11 with the carrier device 12 and the fixing magnet 14 are described in detail with reference to FIGS. 2 to 4. This magnet carrier 11 is a component of all three (different) embodiments. The assembly of the carrier device 12 has essentially two components, namely on the one hand a T-shaped carrier base 18 with the cantilever 10 and on the other hand a (carrier) slider 20 slidably mounted thereon transversely to the longitudinal axis L of the cantilever 10.

The carrier base 18 is, as already explained above, adapted by means of the cantilever 10 to be displaceably hinged to the telescopic rod 4 of the aligning device 1. For an adjustment possibility of an alignment with respect to the aligning device 1, the carrier base 18 comprises the block-shaped or rod-shaped cantilever 10, which forms the long 'T' piece of the T-shaped carrier base 18 and extends rectilinearly away from the slider 20 or fixing magnet 14. The passage slit 22 has rounded end stops 24 that have the same radius as the radius of the telescopic rod 4 in this area.

This allows the telescopic rod 4 to extend through the passage slit 22 and to be guided longitudinally from one end to the other end of the passage slit 22. The outer side surfaces 26 of the cantilever 10 have corrugations or notches 28 along their entire dimension along the longitudinal axis L, which are perpendicular to the longitudinal axis L of the cantilever 10. By means of a positioning clamp (not shown) in cooperation with the notches 28, the telescopic rod 4 can then be positively fixed in its intended position.

The carrier base 18 also has two guide projections or guide bars 30 at its end face, orthogonal to the longitudinal axis L, in a sliding direction V, the guide bars 30 being offset relative to one another on two opposite sides of the carrier base and formed integrally therewith. The two guide bars 30 serve to guide the slider 20, which can slide translationally on a flat sliding surface 32 of the carrier base 18 at the end face thereof. Two opposing guide hooks/grips 34 of the slider 20 each grip around the guide bar 30 so that the slider 20 is guided axially displaceably on the carrier base 18 and does not fall off.

The round fixing magnet 14 is rigidly mounted on the side opposite the grips 34 or on the front side of the slider 20. Alternatively, it is of course also conceivable that the fixing magnet 14 is embedded in the slider 20 or in an indentation in the slider 20 so that it is flush with the slider 20. In particular, the fixing magnet 14 can also be encased by a protective layer in the form of a plastic layer, so that sterilizability is significantly improved.

Figure 5:
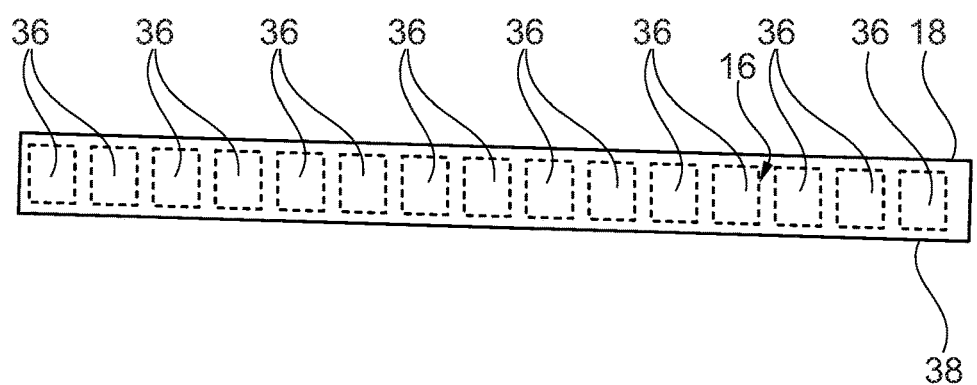
FIG. 5 shows a top view of a slap wrap of the fixing system of the first preferred embodiment.

The slap wrap 16 is shown in FIG. 5 in a first state in which its longitudinal axis runs along a straight line. For magnetization, the slap wrap 16 in this embodiment has magnetic portions distributed along its entire longitudinal axis in the form of bendable magnetic platelets 36, which are inserted or enclosed between two layers of the slap wrap 16. The slap wrap 16 is flat or elongated. This first (open) state of the slap wrap 16 is caused by a geometric restriction that holds the slap wrap 16 in its elongated position against its pretension. Specifically, the slap wrap 16 has a slight bend towards its outer sides 38 when viewed in cross-section along its longitudinal axis. Thus, when viewed in cross-section, the slap wrap 16 is not entirely planar, but rather has a slightly concave or channel-like shape. This channel-like shape prevents the slap wrap 16 from curling. The elongated slap wrap 16 can then be positioned on a tibia or ankle joint of the patient (not shown). If the slight bend in the slap wrap 16 is then manually bent back or retracted, and thus the geometric constraint is withdrawn, the slap wrap winds around the patient's ankle joint due to its material elastic pretension, which it attempts to relieve, and clamps the patient's ankle joint in a force-fit manner. Such a slap wrap 16 has a spiral or helical shape in its untensioned inherent form, as shown in FIG. 2.

The magnetic platelets 36 are discretely spaced along the entire longitudinal axis of the slap wrap 16. These even magnetically support, in addition to the snap action of the slap wrap 16, a clamping closure of the slap wrap 16 lying in a spiral around the ankle joint.

Seen in cross-section, the slap wrap 16 has several layers. An uppermost and lowermost layer serves to delimit the slap wrap 16 from its surroundings and is made of plastic. The planar lowermost and uppermost surfaces can be easily cleaned and sterilized. Between the uppermost and lowermost layers is a snap form, which can be either sheet-like or plastic-like, and can be located radially outwards (see FIG. 2) above this, of one of the flexible magnetic platelets 36. The uppermost and lowermost layers thus completely encase the snap form and the magnetic platelet and delimit them from the outside.

In particular, the fixing system can have 2 different slap wraps 16 of different lengths and, in the spiral state, of different diameters, so that the user is provided with a set in which he can select the appropriate slap wrap 16, depending on the patient's anatomy, so that the diameter corresponds approximately to the diameter of the tibia near the ankle joint.

Such a slap wrap 16 is also inexpensive to produce, since the magnetic platelets 36 for different lengths of slap wraps can always have the same dimensions. Only the number of magnetic platelets 36 varies depending on the length.

The carrier device 12 has a fulcrum shaft 40 as a rotational adjustment for aligning the slider 20 with respect to the carrier base 18. A rotatable threaded pin/threaded spindle 42 with external thread 44 engages in an adapter block with internal thread, which is mounted on the carrier base 18. The threaded pin 42 protrudes through a borehole of a web and is axially fixed to the slider 20 by this web, so that a rotation of the threaded pin 42, corresponding to the pitch of the external thread 44, causes a translational displacement of the adapter block with internal thread and thus of the slider 20 in the sliding direction V. The fulcrum shaft 40 can thus be used to adjust a relative position and thus an alignment of the slider 20 with respect to the carrier base 18. Thus, the fixing system 2 of the aligning device 1 can, among other things, effect an adjustment of the inclination of the guiding device 6 and thus of the guiding gap 8 or of the resection plane.

Figure 6:
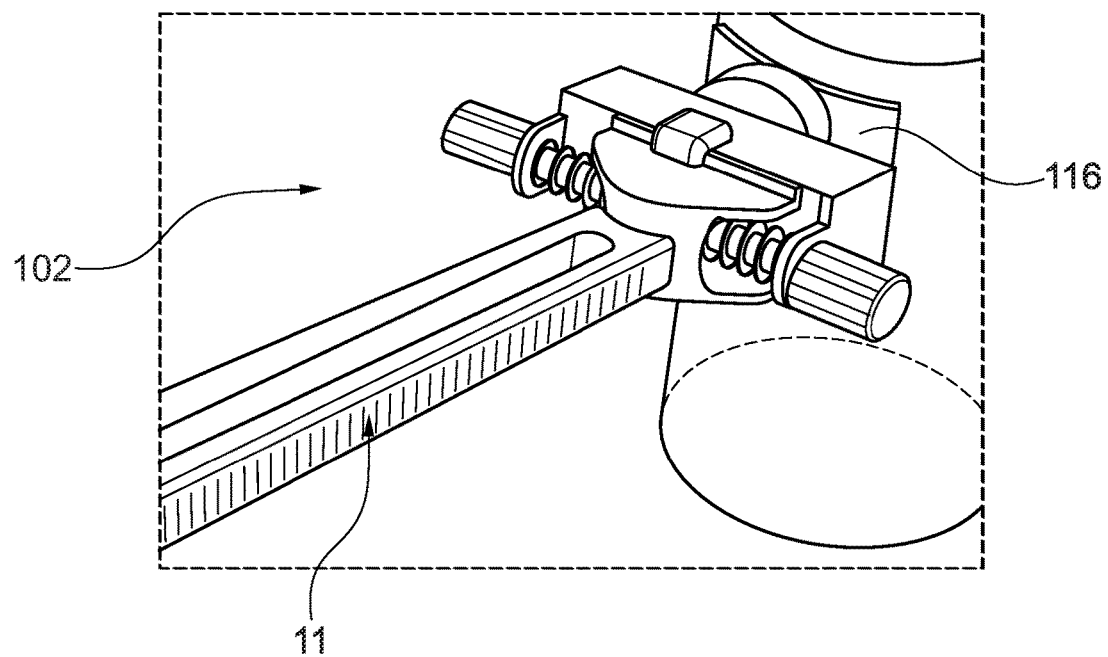
FIG. 6 shows a perspective view of a fixing system of a second preferred embodiment with magnetic foil.

FIG. 6 shows a fixing system 102 according to the invention in accordance with a second preferred embodiment. The magnet carrier 11 with the carrier device 12 and the front-side fixing magnet 14 is again identical to the first embodiment described above, which is why reference is made to the latter. In contrast to the first embodiment of the fixing system 2, the second embodiment of the fixing system 102 now has a magnetic band in the form of a magnetic foil 116 instead of a magnetic band in the form of a slap wrap 16 (see FIG. 5).

The flexible and sheet-shaped magnetic foil 116 has a layer thickness of about 1 mm, is magnetically attracted towards the fixing magnet 14 on the front side and has an adhesive portion in the form of an adhesive layer on the back side. The adhesive layer has a peel-off film protecting the adhesive layer for handling. This allows the user to handle and pre-position the magnetic foil 116 without the magnetic foil 116 sticking unintentionally, and only at the intended shaved body part can the peel-off foil be removed and the flexible magnetic foil 116 applied and adhesively fixed to the patient.

The advantage of the embodiment of the fixing system 102 with magnetic foil 116 is that the magnetic foil 116 can be attached to the patient's ankle or lower tibia regardless of the patient's anatomy. The flexible magnetic foil 116 adapts adaptively to the surface. After resection or surgery, the magnetic foil is peeled off and removed from the patient, similar to a plaster. There are no hematomas and the flexible magnetic foil 116 covers any patient anatomy. The magnetic foil 116 can also be labeled or markings can be painted on it.

Figure 7:
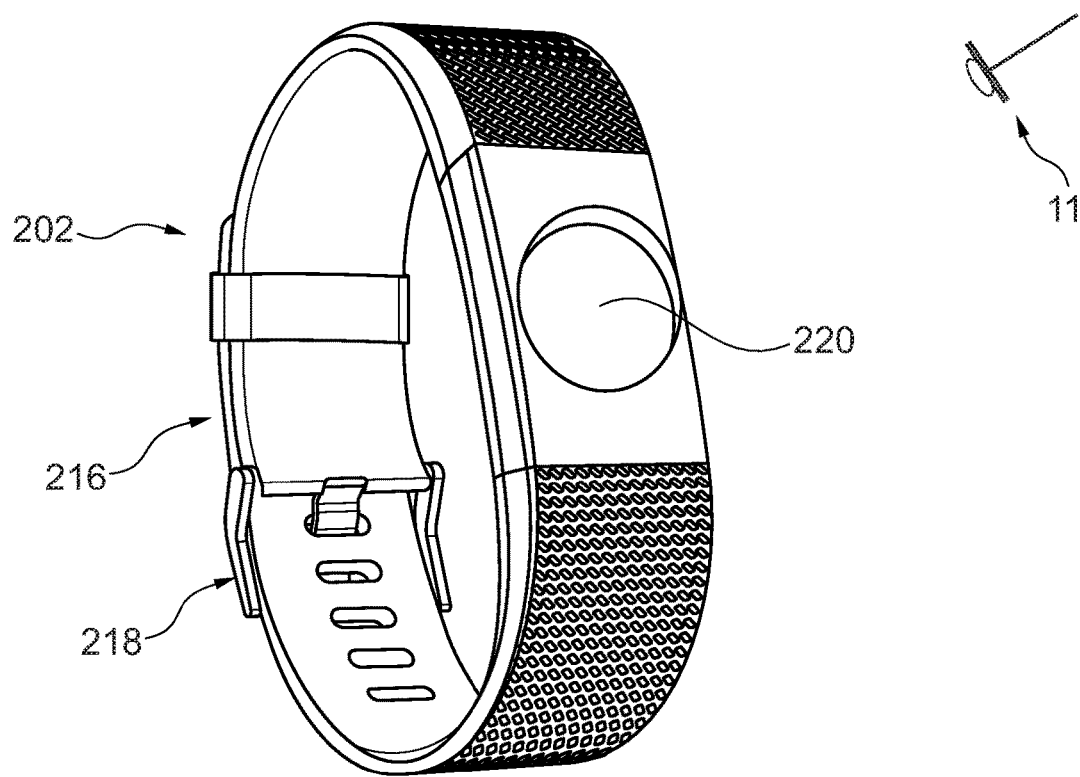
FIG. 7 shows a perspective view of a magnet wrist band of a fixing system according to the invention of a third preferred embodiment.

FIG. 7 shows a fixing system 202 according to the invention in a third preferred embodiment. The fixing system 202 again has the magnetic carrier 11, but now, instead of a magnetic slap wrap 16 or a magnetic foil 116, a magnetic wristband 216 is used as a magnetic band. The magnetic wrist band 216 has, similar to a watch band, a wristband closure 218 adjustable in the circumferential direction and thus in diameter, in order, when applied to an ankle joint, to firmly lash the magnetic wrist band 216 according to the anatomy. The magnetic wristband 216 has a magnetic wristband portion 220 diametrically opposite the closure 218. This is again designed in such a way that, when placed around the patient's ankle, the front side of the magnetic wristband portion 220 facing radially outward is pulled towards the fixing magnet 14.

The advantage of the magnetic wristband 216 is that the magnetic wristband portion 220 is planar in design to be able to stick to the likewise planar fixing magnet 14 better and stronger. In addition, a predetermined magnetic area can be established in advance. In this embodiment, a geometric indentation 222 complementary to the geometric round shape of the fixing magnet 14 is formed in the magnetic wristband portion 220. Thus, the fixing magnet 14 can be precisely positioned in the indentation 222 by the user, and a secure fit is ensured. Of course, it is also possible to design the magnetic wristband 216 without indentation 222 with only a flat surface. This avoids cleaning-intensive undercuts and gives the user an extended adjustment option, since he/she can then position the fixing magnet 14 at different positions in the entire area of the magnetic wristband portion 220.

The magnet inserted in the magnetic portion 220 is flat. The geometric shape of the flexible magnetic wristband 216, on the other hand, conforms to the anatomy of the ankle joint or ankle that it encloses. In particular, a flexible plastic or a flexible rubber coating may be used as the material for the magnetic wristband.

Of course, further types of closure of the magnetic wristband 216 are conceivable. For example, a latching mechanism, another magnetic closure mechanism, a clip-lock closure such as found on backpacks, or similar to a belt, a (closure) buckle or clip-closure can be used.

The invention claimed is:

1. A fixing system for an aligning device of a tibial resection guide for fixating attachment to a limb of a patient, the fixing system comprising:
   a carrier device having an attachment portion for attaching to an adjustment rod;
   a fixing magnet arranged on a face side of the carrier device; and
   a magnetic band comprising a first side adapted to be attracted to the fixing magnet and a second side opposite the first side, the second side having a concave curvature adapted to be attached to the limb of the patient.

2. The fixing system according to claim 1, wherein the magnetic band comprises a magnetic slap wrap having a longitudinal axis that extends along a straight line by a geometric restriction against a pretension in a first state, and that winds around the limb of the patient in a spiral or helical manner in a second state after the geometric restriction has been removed, relieving the pretension and clampingly fixing the magnetic slap wrap.

3. The fixing system according to claim 2, wherein the magnetic slap wrap has a length of at least 300 mm along its longitudinal axis.

4. The fixing system according to claim 1, wherein the magnetic band comprises a magnetic foil, the magnetic foil having a back that has an adhesive portion to be adhered to a body part.

5. The fixing system according to claim 1, wherein the magnetic band comprises a magnetic wristband with a closure, the magnetic wristband being attachable in a wrapping manner to the limb of the patient and configured to be closed and fixed by the closure.

6. The fixing system according to claim 1, wherein the carrier device has a carrier base with the attachment portion and a slider with the fixing magnet, wherein the slider is displaceable translationally in a sliding direction relative to the carrier base.

7. The fixing system according to claim 6, wherein the carrier device has a rotational adjustment mechanism with which the position of the slider relative to the carrier base is adjustable in the sliding direction.

8. The fixing system according to claim 1, wherein the carrier device has a concave holder perpendicular to a longitudinal axis of the attachment portion, in which the fixing magnet is enclosed, so that in addition to a force-fitting fixation, a form fit to sides of a tibial axis is achieved.

9. The fixing system according to claim 1, wherein the attachment portion comprises a cantilever having a passage slit along its longitudinal axis for displaceably accommodating an adjustment rod in a direction of the longitudinal axis.

10. An aligning device for a tibial resection guide having an adjustment rod configured to be arranged at a patient's tibia and having a guiding device at a proximal end of the adjustment rod for guiding a tool during a resection of the patient's tibia, the aligning device comprising a fixing system according to claim 1 arranged at a distal end of the adjustment rod or towards the distal end of the adjustment rod.

11. A fixing system for an aligning device of a tibial resection guide for fixating attachment to limbs, the fixing system comprising:
    a carrier device having an attachment portion for attaching to an adjustment rod;
    a fixing magnet arranged on a face side of the carrier device; and
    a magnetic band adapted to be attracted to the fixing magnet and adapted to be attached to limbs of a patient,
    wherein the magnetic band comprises a magnetic foil, the magnetic foil comprising a back having an adhesive portion to be adhered to a body part.

12. The fixing system according to claim 11, wherein the carrier device has a carrier base with the attachment portion and a slider with the fixing magnet, wherein the slider is displaceable translationally in a sliding direction relative to the carrier base.

13. The fixing system according to claim 12, wherein the carrier device has a rotational adjustment mechanism with which the position of the slider relative to the carrier base is adjustable in the sliding direction.

14. The fixing system according to claim 11, wherein the carrier device has a concave holder perpendicular to a longitudinal axis of the attachment portion, in which the fixing magnet is enclosed, so that in addition to a force-fitting fixation, a form fit to sides of a tibial axis is achieved.

* * * * *